United States Patent
Stålemark et al.

(10) Patent No.: US 6,827,727 B2
(45) Date of Patent: Dec. 7, 2004

(54) METHOD AND DEVICE FOR APPLYING EXTERNAL PRESSURE IN COMBINATION WITH COAGULANT TREATMENT OF PUNCTURE WOUNDS

(75) Inventors: Jan Stålemark, Täby (SE); Torbjörn Mathisen, Älvsjö (SE)

(73) Assignee: Radi Medical Systems AB, Uppsala (SE)

( * ) Notice: Subject to any disclaimer, the term of this patent is extended or adjusted under 35 U.S.C. 154(b) by 359 days.

(21) Appl. No.: 10/020,495

(22) Filed: Dec. 18, 2001

(65) Prior Publication Data

US 2003/0114881 A1 Jun. 19, 2003

(51) Int. Cl.⁷ .............................................. A61B 17/00
(52) U.S. Cl. ...................................... 606/201; 606/203
(58) Field of Search .................... 606/201–203; 600/490, 499; 128/961, 100.1, 112.1

(56) References Cited

U.S. PATENT DOCUMENTS

| | | | |
|---|---|---|---|
| 3,533,940 A | 10/1970 | Peniston et al. | 210/52 |
| 4,798,199 A | 1/1989 | Hubbard et al. | 128/87 R |
| 4,957,105 A | 9/1990 | Kurth | 128/96.1 |
| 5,307,811 A | 5/1994 | Sigwart et al. | 128/677 |
| 5,308,622 A | 5/1994 | Casscells et al. | |
| 5,569,297 A | 10/1996 | Makower et al. | 606/201 |
| 5,571,181 A * | 11/1996 | Li | 623/23.75 |
| 5,601,597 A | 2/1997 | Arrowood et al. | 606/203 |
| 5,741,283 A | 4/1998 | Faby | |
| 5,792,173 A * | 8/1998 | Breen et al. | 606/201 |
| 5,799,650 A | 9/1998 | Harris | 128/96.1 |
| 5,997,564 A | 12/1999 | Shehata et al. | 606/201 |

FOREIGN PATENT DOCUMENTS

| | | |
|---|---|---|
| GB | 2314856 A | 1/1998 |
| WO | WO 96/25110 A1 | 8/1996 |

OTHER PUBLICATIONS

Klokkevold, "The Effect of Poly–N–Acetyl Glucosaminoglycan (Chitosan) on Osteogenesis in vitro," Klokkevold Thesis (1995), http://dent.ucla.edu/pic/members/theses/klokkevold/klokkevold.thesis.html.

Dun & Bradstreet Report, Jan. 9, 2002.

* cited by examiner

Primary Examiner—Kevin T. Truong
(74) Attorney, Agent, or Firm—Foley & Lardner LLP

(57) ABSTRACT

Following a catheterisation of the artery, the flow of blood through the puncture wound has to be stopped. With the method according to the invention, the time for achieving haemostasis can be reduced by combining the normal clotting mechanism with a chitosan induced clogging mechanism. A compression device (1; 8; 16) for achieving haemostasis in a puncture wound comprises a compressor (2; 9; 17) and a pressure element (3; 10; 18) connected to said compressor (2; 9; 17) so that the bottom side of the pressure element (3; 10; 18) is in contact with the puncture wound, characterized in that the bottom side of the pressure element (3; 10; 18) is provided with chitosan, so that the chitosan and the external compression pressure are applied simultaneously on the puncture wound when the compressor (2; 9; 17) applies an external compression pressure on the puncture wound via the pressure element (3; 10; 18).

8 Claims, 3 Drawing Sheets

METHOD AND DEVICE FOR APPLYING EXTERNAL PRESSURE IN COMBINATION WITH COAGULANT TREATMENT OF PUNCTURE WOUNDS

FIELD OF THE INVENTION

The present invention relates in general to a method for achieving haemostasis by applying an external compression pressure on a puncture wound in combination with a coagulant treatment of said puncture wound. The invention also relates to a device with which the coagulant and the external compression pressure can be applied simultaneously on the puncture wound.

BACKGROUND OF THE INVENTION

Following an invasive medical procedure, such as catheterisation or similar invasive medical procedure, the flow of blood through the puncture wound has to be stopped, so that haemostasis can begin as soon and fast as possible after the completion of the invasive medical procedure. Several devices have been suggested that facilitate and accelerate this haemostasis by providing a compression pressure that compresses the blood vessels at the puncture site to stop the flow of blood therethrough. Examples of femoral compression devices may be found in the U.S. Pat. Nos. 4,957,105, 5,307,811, 5,799,650 and 5,997,564, while examples of devices for the compression of the radial artery may be found in U.S. Pat. Nos. 4,798,199, 5,569,297 and 5,601,597. The entire contents of all of these patents are incorporated herein by reference.

Although there exist numerous compression devices having very different designs and types of mechanical or pneumatical pressure applying means, the basic working principle is the same: a pressure element is positioned at the wound site and some kind of compressing means is provided which presses the pressure element against the puncture wound, thereby stopping the flow of blood therethrough so that haemostasis can begin. Normally it takes about 20 minutes to achieve haemostasis. If, however, a patient has been given heparin to, for example, avoid blood clots, the time for achieving haemostasis may be as long as 1.5 hours. Besides being uncomfortable for the patient and being expensive for the medical service, a long compression time involves the risks of vein thrombosis, tissue necrosis, nervous damages, and other more or less severe complications.

In the case described above, the underlying process for haemostasis is the so-called normal clotting mechanism, which basically involves three steps: 1) a complex substance called prothrombin activator is formed, 2) prothrombin activator converts a plasma protein called prothrombin into thrombin, and 3) thrombin catalyses the joining of fibrinogen molecules present in plasma to a fibrin mesh, which traps blood cells and effectively seals the wound until the blood vessel can be permanently repaired (see E. N. Marieb, Human Anatomy and Physiology, 3rd ed., The Benjamin/Cummings Publishing Company, CA, 1995, p. 601).

Since it takes a certain amount of time before haemostasis is achieved by means of the normal clotting mechanism, there also exists a corresponding minimal compression time, i.e. the time during which the compression device has to be arranged around a part of the patient's body. This compression time is, of course, dependent on several different factors, which vary from patient to patient, such as the specific puncture site and size, different blood related parameters, if heparin or some other anticoagulants are used, etc. Nevertheless, for a given patient, a minimal compression time exists for achieving haemostasis.

SUMMARY OF THE INVENTION

In order to further reduce the compression time, a compression device can be combined with some other means that produces haemostasis via a mechanism which is different from the normal clotting mechanism. Such a haemostatic agent is chitosan, which is a collective term applied to deacetylated chitins in various stages of deacetylation and depolymerisation. Chitin is the structural polymer of the exoskeleton of arthropods and cell walls of fungi. These are linked by Beta 1–4 glycosidic bonds into a linear polymer containing hundreds or thousands of units. The technology for the preparation of chitosan is described in U.S. Pat. No. 3,533,940. The entire contents of this patent are incorporated herein by reference. Several studies have shown that chitosan achieves haemostasis independent of normal clotting mechanisms via cellular aggregation or clogging (see P. R. Klokkevold, The Effect of Poly-N-Acetyl Glucosaminoglycan (Chitosan) on Osteogenesis in vitro, Thesis, UCLA, LA, 1995). Herein the mechanism(s) with which chitosan is achieving haemostasis is referred to as the clogging mechanism.

By providing the pressure element of a compression device with an active layer of chitosan, it is therefore possible to combine the normal clotting mechanism and the clogging mechanism, thereby reducing the time during which the compression device has to be arranged around a part of the patient's body. This combined method can be extremely valuable when the normal clotting mechanism is absent or reduced due to, for example, a heparin treatment of the patient.

The present invention thus provides a method for achieving haemostasis, wherein the normal clotting mechanism is combined with the chitosan induced clogging mechanism. The invention also provides a method for achieving haemostasis when the effect of the normal clotting mechanism is reduced or absent. Chitosan and an external compression pressure can be applied simultaneously on a puncture wound.

A compression device according to the present invention comprises a compressor connected to a pressure element having a side provided with chitosan. The compressor may comprise an adjustable belt or clamp to be arranged around a part of the patient's body. In use, the chitosan side of the pressure element is placed in contact with the puncture wound, and the compressor is operated for applying an external compression pressure on the pressure element, which, in turn, presses against the puncture wound. The chitosan is released into the blood and tissue of the patient, and it is therefore possible to obtain haemostasis by means of the combined effects of the normal clotting mechanism and the clogging mechanism, thereby reducing the time during which the compression device has to be arranged around a part of the patient's body.

DETAILED DESCRIPTION OF THE PREFERRED EMBODIMENTS

The method according to the present invention is applicable on all different types of bleeding wounds, although the most anticipated use is to stop the bleeding following a catheterisation or similar invasive medical procedure. A catheterisation of, for example, the heart is normally done via the femoral artery in the groin or via the radial artery at the inner wrist. A corresponding device, with which the present method can be executed, is therefore adapted to be positioned at the femoral artery or at the radial artery, respectively. In the description below, three different embodiments of the inventive device are described, one for femoral compression and two for radial compression.

Figure 1:
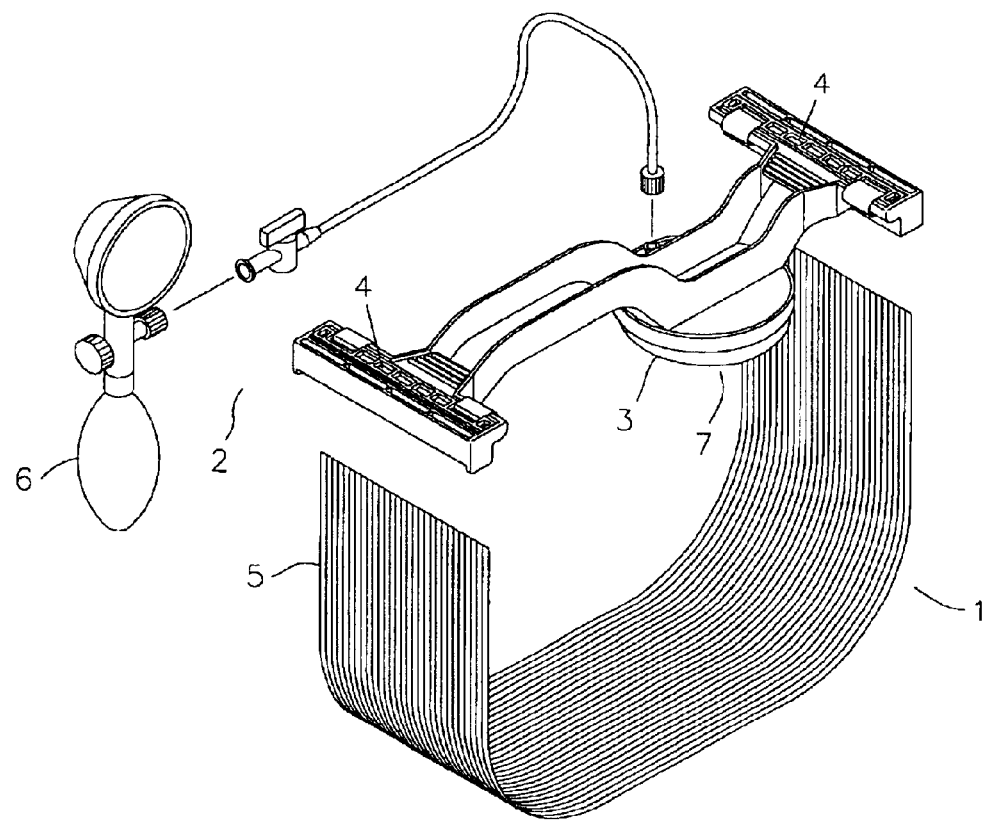
FIG. 1 shows a preferred embodiment of a femoral compression device according to the invention.
Figure 2:
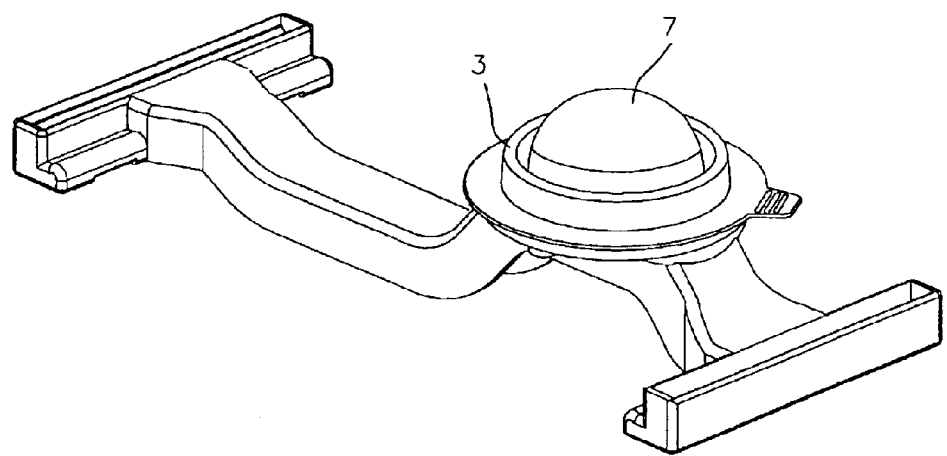
FIG. 2 is a top view of the femoral compression device of FIG. 1.

FIG. 1 shows a preferred embodiment of a femoral compression device 1 comprising a compressor 2 and an inflatable pressure element 3. The compressor 2 comprises a base plate 4, a belt 5, which is adapted to be fixed around a patient's body, and a pump 6 connected to the inflatable pressure element 3. The base plate 4 has a top portion and a bottom portion and is adapted to be fixed to the belt 5. The inflatable pressure element 3 is provided at the bottom portion of the base plate 4. As is best seen in FIG. 2, the bottom side of the pressure element 3 is coated with a layer 7 of chitosan. In use, the pressure element 3 is positioned so that the chitosan layer 7 is in contact with the puncture wound, the belt 5 is then tightened around the patient's body, and the inflatable pressure element 3 is inflated by the pump 6, thereby applying a compression pressure at the wound site. When the chitosan is released into the blood and tissue of the patient, it is possible to achieve haemostasis be means of the combined effects of the normal clotting mechanism and the clogging mechanism.

Figure 3:
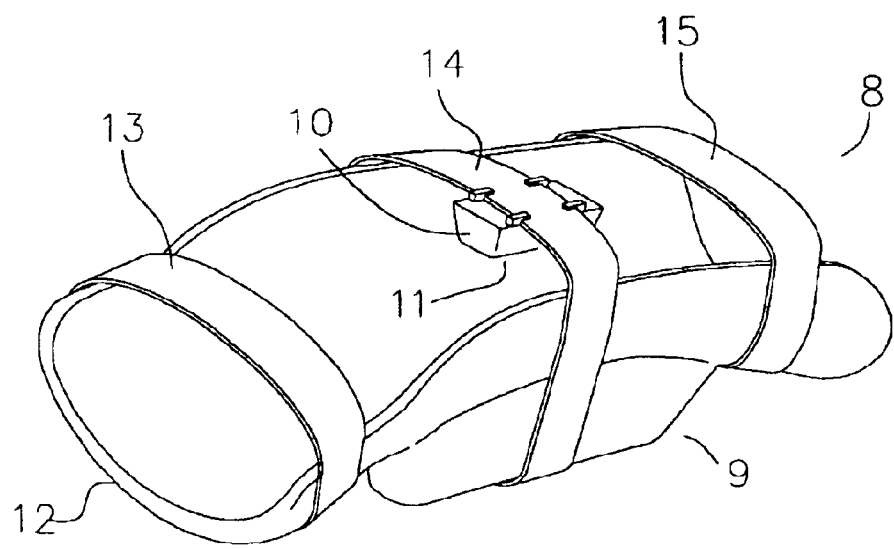
FIG. 3 shows a preferred embodiment of a radial compression device according to the invention.

A first embodiment of a radial compression device 8 is illustrated in FIG. 3. The radial compression device 8 comprises a compressor 9 and a pressure element 10, the bottom side of which is coated with a layer 11 of chitosan. The compressor 9 comprises a support plate 12 and a plurality of securing straps 13, 14, 15. The first strap 13 is provided at the distal end of the support plate 12 for securing the fingers and palm of a patient's hand. The second strap 15 is provided at the proximal end of the support plate 12 for securing the support plate 12 to the lower part of the patient's forearm. The third strap 14, on which the pressure element 10 is provided, is arranged between the first and second straps 13, 15, approximately in the middle of the support plate 12. In use, the pressure element 10 is positioned so that the chitosan layer 11 is in contact with the puncture wound and the support plate 12 is arranged essentially on the opposite side of a patient's wrist, the first and second securing straps 13, 15 are then tightened to hold the support plate 12 in place, and finally the third securing strap 14 is tightened, thereby applying a compression pressure at the wound site.

Figure 4:
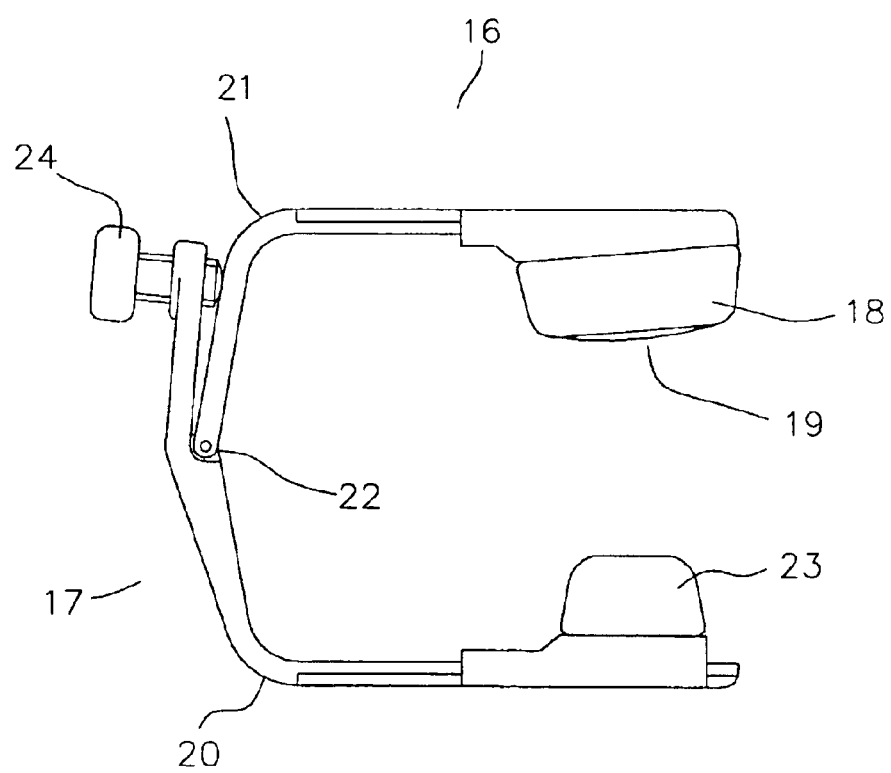
FIG. 4 shows an alternative embodiment of a radial compression device according to the invention
Figure 5:
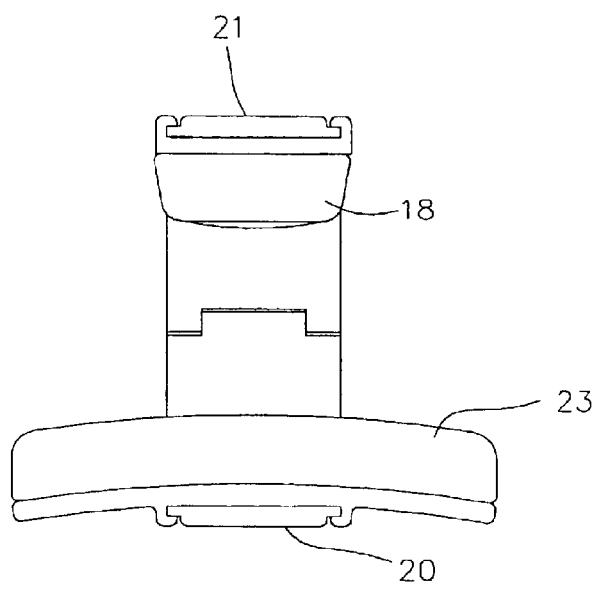
FIG. 5 is an end view of the radial compression device of FIG. 4.

FIG. 4 and FIG. 5 illustrate another embodiment of a radial compression device 16. The radial compression device 16 comprises a compressor 17 and a pressure element 18, the bottom side of which is coated with a layer 19 of chitosan. The compressor 17 comprises a support arm 20 and a compression arm 21, which form a C-shaped clamp. The support arm 20 and the compression arm 21 are pivotally connected in a hinge joint 22 in such a way that the proximal end of the support arm 20 extends behind the compression arm 21. At the distal end, i.e. the end remote from the hinge joint 22, the inside of the support arm 20 is provided with a support pad 23, and the opposing pressure element 18 is provided on the distal end of the compression 21. A clamping screw 24 is threaded through the proximal end of the support arm 20 in such a way that the front end of the clamping screw 24 is in contact with the compression arm 21. By screwing the clamping screw 24 inwards or outwards, the distance between the support pad 23 and the pressure element 18 can be adjusted, thereby controlling the compression pressure applied on the radial artery. Although the clamping screw 24 is a convenient pressure-adjusting mechanism 24 to adjust the distance between the pressure element 18 and the support pad 23, there exist other ways to a accomplish this distance adjustment (and thereby pressure adjustment), such as spring-loaded means, cogged or toothed means. It is also possible to have an inflatable pressure element and/or and inflatable support pad, so that the distance between the pressure element and the support pad can be adjusted by expanding the pressure element and/or the support pad by means of a pneumatic device.

Figure 6:
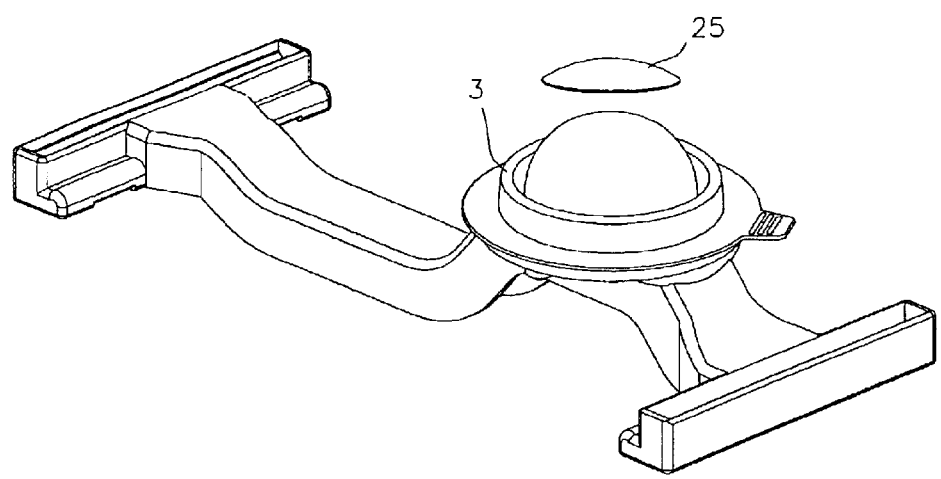
FIG. 6 shows another embodiment of the invention.

In the embodiments shown above, the bottom sides of the pressure elements are coated with chitosan, i.e. the term "coated" implies that a layer of chitosan is applied directly on the bottom side of the pressure element in question. It is, however, also possible to use a separate, chitosan coated or soaked patch or a patch made of chitosan, which is provided between the puncture site and the bottom side of the pressure element. In this patent specification and in the claims "chitosan patch" means a chitosan coated or soaked patch or a patch made of chitosan. This chitosan patch could be provided separately and manually between the puncture site and the bottom side of the pressure element, although it is preferred to provide the pressure element with the chitosan patch already applied during the manufacture of the compression device. In FIG. 6, a chitosan patch 25 is shown together with a femoral compression device of the type shown in FIG. 1 and FIG. 2. The chitosan patch 25 is shown prior to attachment to the pressure element 3 of the femoral compression device, but it is to be understood that the chitosan patch 25, with suitable modifications, could be used together with any of the embodiments of the compression devices described above. It is also possible to have a separate chitosan patch 25, which is placed at the puncture wound before the pressure element is positioned over the puncture site.

If the chitosan patch is attached to pressure element during assembly of the corresponding compression device, the chitosan patch is advantageously a releasable or detachable patch, which remains seated to the puncture wound when the compression device and the corresponding pressure element are removed from the puncture site. The chitosan patch could be in the form of a weakly adhesive patch, which is attached to the bottom side of the pressure element. When the compression device is to be removed from the puncture site, the surgeon keeps the chitosan patch in place by holding an edge of the chitosan patch pressed down towards the puncture site, and then removes the pressure element and the corresponding compression device. In this case, the chitosan patch should only adhere weakly to the bottom side of the pressure element, i.e. a weak adhesive should be used. It is also possible to let the chitosan patch adhere to the bottom side of the pressure element by means of covalent forces, which attract the chitosan patch to the bottom side of the pressure element. As a comparison, it is covalent forces that adhere a thin plastic film to a surface. In this case, the chitosan patch should be in the form of a thin film or foil of a suitable material, such as plastic.

Although the present invention has been described with reference to specific embodiments, also shown in the appended drawings, it will be apparent to those skilled in the art that many variations and modifications can be done within the spirit and scope of the invention. For example, coagulants other than chitosan (e.g., thrombine) may be employed in the invention. Thrombine is a very strong coagulant which achieves haemostasis via the normal clotting mechanism (as opposed to the clogging mechanism).

What is claimed is:

1. A compression device for achieving haemostasis in a puncture wound following a catheterisation procedure, comprising:
    a compressor; and
    a pressure element connected to said compressor so that a side of the pressure element is in contact with said puncture wound, wherein said side of the pressure element is provided with coagulant, so that the coagulant and external compression pressure are applied simultaneously on said puncture wound when said compressor applies external compression pressure on said puncture wound via said pressure element; and
    wherein the coagulant is provided at said side of the pressure element by a coagulant patch, which is detachable from the pressure element, so that the coagulant patch remains seated at the puncture wound when the pressure element is removed.

2. A compression device according to claim 1, wherein the coagulant patch is in the form of a weakly adhesive patch, an adhesive side of which is attached to said side of the pressure element and which is easy to remove therefrom.

3. A compression device according to claim 1, wherein the coagulant patch is in the form of a thin foil, which adheres to said side of the pressure element by covalent forces and which is easy to remove therefrom.

4. A compression device according to claim 1 for the compression of the femoral artery, which femoral wherein further comprises an inflatable pressure element and the compressor comprises a belt adapted to be fixed around a patient's body, a base plate, which is connectable to the belt and has a top portion and a bottom portion connected to the pressure element, and a pump connectable to the pressure element, wherein external compression pressure are applied simultaneously on said puncture wound when the inflatable pressure element is inflated by the pump.

5. A compression device according to claim 1 wherein further and comprising a support plate having a first securing strap connected to a distal end of the support plate, a second securing strap connected to a proximal end of the support plate, and at least one intermediate securing strap, on which the pressure element is attached, for holding the pressure element and the support plate in position on essentially opposite sides of the wrist of a patient, wherein the coagulant and external compression pressure are applied simultaneously on said puncture wound when said at least one intermediate securing strap is tightened.

6. A compression device according to claim 1 wherein further comprises compression of the radial artery, which wherein further comprises a support arm provided with a support pad, a compression arm connected to the support arm and provided with the pressure element, and a pressure-adjusting assembly for adjusting the distance between the support pad and the pressure element, so that, when the compression device is arranged on a forearm of a patient, the support pad bears against a well-defined area at the upside of the radius bone and the pressure element bears against a well-defined area at the underside of the radius bone, wherein the coagulant and external compression pressure are applied simultaneously on said puncture wound by the pressure-adjusting assembly.

7. A compression device according to claim 1, wherein the coagulant comprises chitosan.

8. A compression device according to claim 1, wherein the pressure element comprises an inflatable pressure element.

* * * * *